United States Patent [19]

Allen et al.

[11] Patent Number: 4,574,645
[45] Date of Patent: Mar. 11, 1986

[54] APPARATUS FOR SAMPLING PARTICULATE MATERIAL

[75] Inventors: James M. Allen; Thomas B. Howard, both of Green Bay, Wis.

[73] Assignee: James River-Norwalk, Inc., Norwalk, Conn.

[21] Appl. No.: 639,274

[22] Filed: Aug. 9, 1984

[51] Int. Cl.⁴ .............................................. G01N 1/20
[52] U.S. Cl. .............................. 73/863.51; 73/863.56; 73/863.58; 73/863.81
[58] Field of Search ........... 73/863.56, 863.57, 863.58, 73/863.81, 864.73, 863.52, 863.53, 863.51, 863.83

[56] References Cited

U.S. PATENT DOCUMENTS

| | | | |
|---|---|---|---|
| 888,471 | 5/1908 | Constant | 73/863.56 |
| 2,683,373 | 7/1954 | Gallup et al. | |
| 3,060,746 | 10/1962 | Gompper | 73/863.56 |
| 3,138,590 | 6/1964 | Welty et al. | 73/863.56 X |
| 3,241,371 | 3/1966 | Horeth | 73/863.57 X |
| 3,595,087 | 7/1971 | Storks | 73/863.56 X |
| 4,055,088 | 10/1977 | Diss | 73/863.56 |

FOREIGN PATENT DOCUMENTS 145424 12/1980 German Democratic Rep. .................... 73/863.56

Primary Examiner—Stewart J. Levy
Assistant Examiner—Tom Noland
Attorney, Agent, or Firm—W. A. Aguele; H. W. Hargis, III

[57] ABSTRACT

An apparatus for sampling particulate material, such as wood chips as they fall through an unloading chute, includes a tube mounted in a wall of the chute and having an upper end extending into the path of chip flow. The upper end includes a generally semi-cylindrical extension terminating in a generally quarter-spherical section in provision of a chip receiving opening to one side of the tube and a chip deflector to the opposite side of the tube. The lower end of the tube extends outside the chute and communicates with a chip-collecting container, and the tube is selectively rotatable by a timed motor and gear arrangement to present the one side of the tube upwardly to receive chips for sampling or the other side upwardly to deflect chips and prevent their entry into the tube for collection in the chip container.

7 Claims, 4 Drawing Figures

APPARATUS FOR SAMPLING PARTICULATE MATERIAL

BACKGROUND OF THE INVENTION

This invention relates to apparatus for sampling particulate material, especially wood chips as they are being fed downwardly through a chute or the like.

Wood chips arrive at wood pulping facilities usually in carload lots. Due to the large quantities involved, and the manner of shipment, it has been found difficult to sample the chips with sufficient reliability to ensure adequate quality control. One manner of sampling has been the removal of a quantity of chips from the carload, prior to unloading. Another manner of sampling has been to intercept a quantity of chips as they pass through an unloading chute. Methods such as these have involved random, manual sampling, leading to unreliable analysis of the makeup of a chip lot.

Prior art apparatuses have been directed to automatic sampling of granular, or particulate materials in lots of different particle sizes but generally similar particle shapes. The following U.S. patents are representative of apparatuses for automatic sampling of the aforementioned types of materials:

U.S. Pat. No. 3,595,087 discloses apparatus for removing samples of granular material flowing through a horizontally extending conduit 2. The apparatus includes (FIG. 1.) a rotatable and reciprocable tube 6 extending with acute angularity through the conduit wall 14, and presented upstream as respects material flow. The end 8 of the tube 6 is cut on a bias, so that manual rotation of the tube between fixed positions controls the rate of material flow into end 8 of the sample tube 6, flow through the tube being controlled by a valve 32. Reciprocal positioning of the tube vertically compensates for variation in material density due to horizontal flow.

U.S. Pat. No. 3,138,950 discloses apparatus for sampling particulate material including (FIG. 2.) a rotatable probe 50 having an opening. The probe may be rotated between an open position with the opening facing upstream, in a horizontal transfer line 11 of a pneumatic transfer system, and a closed position with the opening facing downstream. The probe is rotated through gearing 51, 52, by motor 53.

U.S. Pat. Nos. 888,471 and 3,060,746 disclose additional examples of sampling apparatus having rotatable elements movable between opened and closed positions within streams of particulate material.

U.S. Pat. No. 2,683,373 discloses an apparatus for sampling grain flowing gravitationally through a pipe 34, including a slidable and rotatable cup 11 movable into and out of the stream of grain through an opening 32 in pipe wall 33. The cup 11 faces upwardly in pipe 34 to fill and while it is moved out to a position above container 35. While above the container the cup is inverted so that the collected grain sample falls into container 11.

None of the prior art disclosures teaches an apparatus for automatically sampling particulate material such as wood chips undergoing downward flow, and which characteristically vary in shape and size.

It is an objective of the present invention to provide an improved apparatus for sampling wood chips.

It is a further, more specific objective to provide a sampling probe that is solely rotational in provision of opened and closed positions, and wherein the opened position accommodates flow of the sampled downwardly flowing chips directly into a collecting container.

SUMMARY OF THE INVENTION

In achievement of the foregoing as well as other objectives, the present invention contemplates improved apparatus for sampling irregularly shaped and sized particulate material, for example wood chips as they are fed downwardly through an unloading chute or the like, wherein improvement resides in an open ended tube extending upwardly through a wall of the chute with acute angularity to the path of the flow of the chips, the one open end of the tube being at a level above the level of the other open end of the tube, and including an extension in the path of flow defined by a generally semi-cylindrical wall section coaxial with the tube and terminating in a generally quarter-spherical wall section, said semi-cylindrical and quarter-spherical wall sections being cooperatively disposed to define a concave chip-receiving probe surface when presented upwardly in a sampling mode and a convex chip deflecting surface substantially coextensive with and facing oppositely from said probe surface when presented downwardly in a non-sampling mode, and means for mounting said tube for rotation about its polar axis in selective provision of said recited modes of presentation of said one end.

The manner in which the foregoing objectives and apparent advantages of the invention may best be achieved will be more fully understood from the following description, taken in light of the accompanying drawing.

DESCRIPTION OF THE PREFERRED EMBODIMENT

Figure 1:
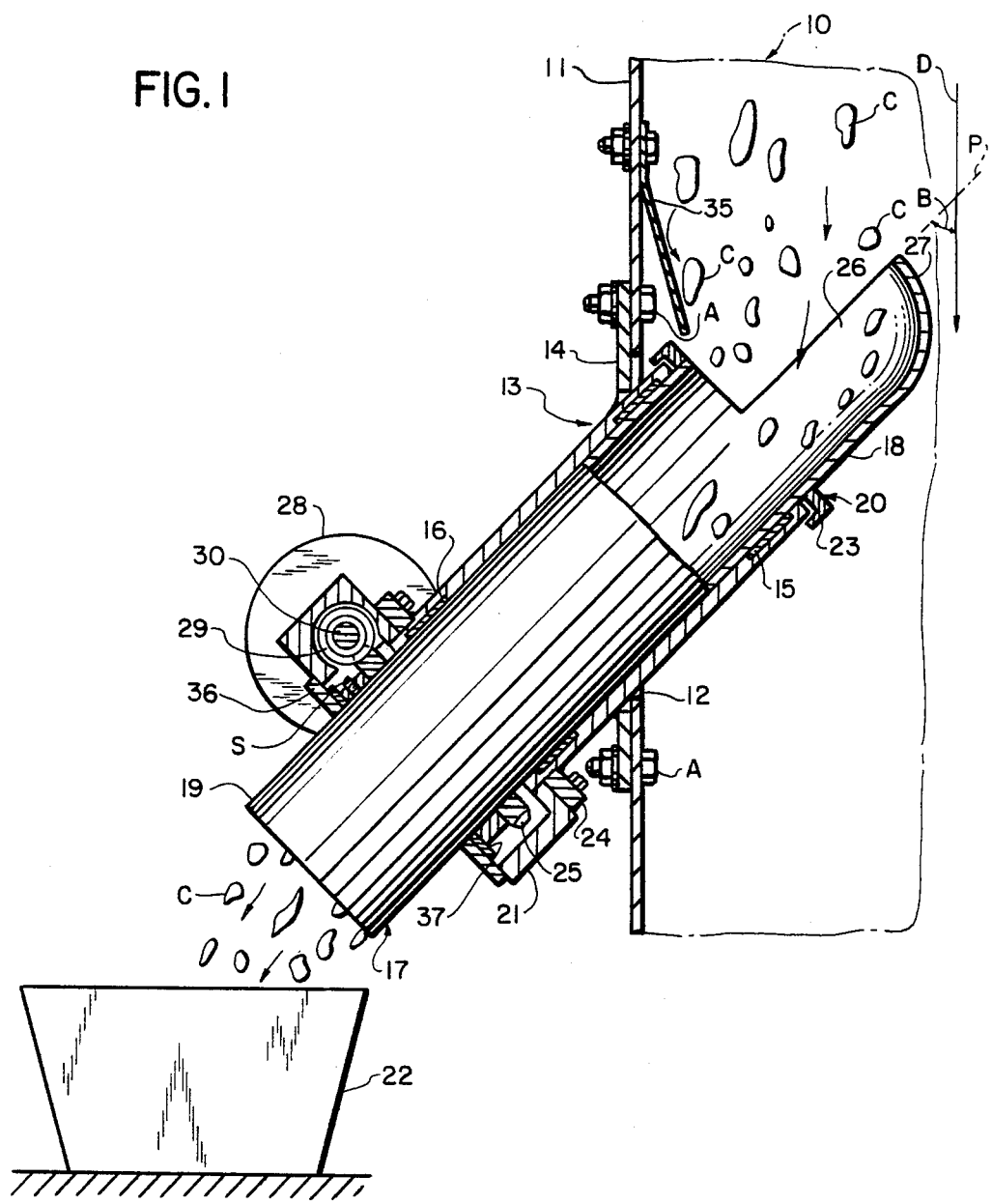
FIG. 1 is an elevational view, partly in section and with parts broken away for the sake of convenience, of a wood chip sampling apparatus embodying the invention, in one of its modes of operation.
Figure 1A:
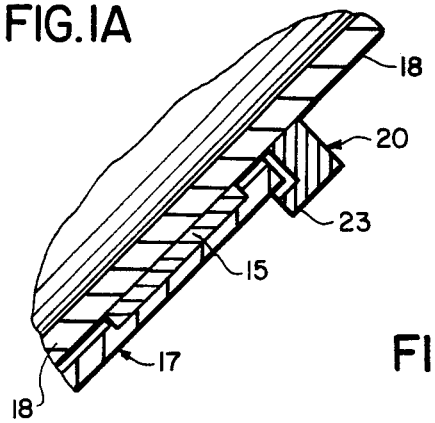
FIG. 1A is an enlarged fragmentary showing of a detail of construction of the apparatus and illustrated in FIG. 1.

With more detailed reference to the drawings, in FIG. 1 a gravitational-flow chip feed chute 10 is defined at least in part by a generally upwardly extending wall section, for example vertical wall 11, having an opening 12. A tubular frame 13 is constructed so that its polar axis P extends with acute angularity of about 45° to the vertical extent of wall 11, and is bolted by a flange 14 thereon to wall 11. With reference also to FIG. 1A, bearing means such as nylon bushings 15 and 16 in tubular frame 13 rotationally support an open ended tube 17 coaxial with the frame, one open end 18 of the tube being disposed in the flow path of chips C falling downwardly in chute 10, and the other open end 19 being outside chute 10 at a level below the level of open end 18. Due to the substantially vertical flow path D of the gravitationally falling chips, the polar axes P of tube 17 and frame 13 also extend with the same acute angularity to the chip flow path D. It will of course be understood that a selected flow path D for the falling chips may be other than vertical, so long as the path has a substantial vertical component, and such variation may be accommodated by positioning the tube 17 with sufficient acute angularity to the vertical component to ensure free passage of the chips through the tube in its open mode and to prevent entry of chips therein in its closed mode.

The upper end 18 of tube 17 includes a releasably mounted ring 20 provided with a flange 23 overlapping an adjacent upper end of frame 13 to function as a dust cap protective of the bushings 15 and 16 against contaminants such as dust, sand, and the like. An annular housing 21 is affixed to the lower end of frame 13 by bolting to a flange 24, and partially encloses a worm gear 25 on tube 17. The housing 21 has a flange fastened thereto, for example by bolts (not shown), and is provided with a thrust bearing surface 37 that engages a confronting bearing surface on worm gear 25 to absorb downward axial thrust of the tube 17 in support of the same in frame 13.

The region of upper open end 18 of cylindrical tube 17 has an extension in the path of chip flow defined by a generally semi-cylindrical wall section 26 coaxial with tube 17 and having a generally quarter-spherical wall section 27 on the free end of section 26. The wall sections 26 and 27 are so cooperatively disposed as to form a rounded, concave chip-receiving probe when the open sides of the sections are presented upwardly in a sampling mode, and a rounded, convex chip deflecting surface when the same open sides are presented downwardly in a non-sampling mode.

A suitable chip collecting container 22 is positioned beneath the lower open end of tube 17 for receiving and storing chip samples.

A driving motor 28 on a suitable support of conventional construction (not shown) has a worm 29 on its shaft 30. Worm 29 is drivingly meshed with worm gear 25, and is disposed within a suitably formed portion of housing 21. The drive motor 28 is powered from a suitable voltage source V, and is selectively energized and deenergized through manual operation of a switch 31. In provision of automatic energization and de-energization of motor 28, a switch 33 activatable by a timer motor 32 is disposed in parallel electrical circuit with manual switch 31. Timer motor 32 also is powered from voltage source V, selectively through a selector switch 34 in series electrical circuit with one side of the voltage source V and motor 32. The timer motor and timer switch apparatus is conventional, and commercially available timers of the programmable type can be used to advantage.

From the foregoing description, it will be appreciated that the sampling apparatus advantageously is unitary therefore being readily installable or removable, as may be required for servicing, repair, or replacement. Removal of the unit is afforded by removal of mounting bolts A extending through flange 14. Removal of tube 17 from frame 13 may be achieved by releasing flange 36 from housing 21, removing dust cap 20 and sliding the tube 17 and worm gear 25 thereon from frame 13. The worm gear 25 is held about tube 17 by set screws, one of which is seen at S, and it may be removed by release of same.

Figure 2:
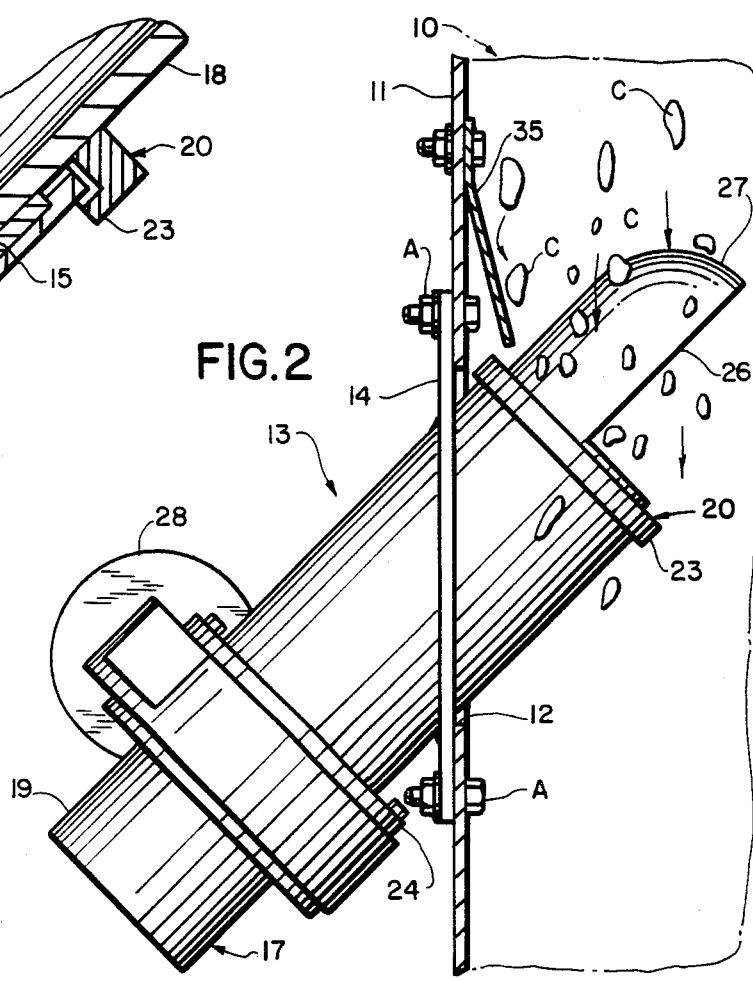
FIG. 2 is an elevational showing similar to FIG. 1, with additional parts in section and showing the sampling apparatus in another of its modes of operation.
Figure 2:
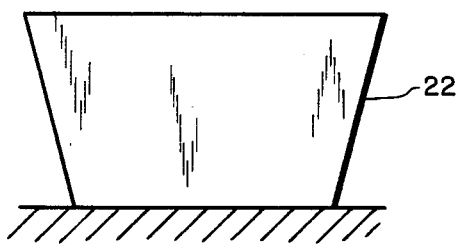
Figure 3:
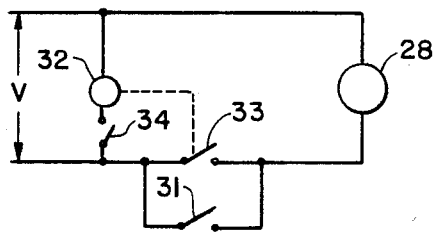
FIG. 3 is a diagrammatic showing of an electrical drive and control means for the apparatus shown in FIGS. 1 and 2.

In operation of the apparatus, and assuming first that no chip samples are to be taken, as is seen in FIG. 2 the tube 17 will have been rotated to the position illustrated, either by automatic closing and opening of timer switch 33 (FIG. 3), with selector switch 34 closed and manual switch 31 opened; or by manual closing and opening of switch 31, while the timer motor 32 is deenergized by virtue of opened switch 34, and with timer switch 33 opened.

Further to the illustrated position of FIG. 2, the upper, open end of tube 17 is presented downwardly so that the inverted cylindrically and spherically shaped sections 26 and 27 defining the opening serve as an upwardly convex deflecting surface for chips C as they fall freely through chute 10. By deflecting the chips, their flow through the tube 17 into container 22 is prevented, hence separate valving for that purpose is advantageously unnecessary.

Assuming now that chip samples are to be taken, drive motor 28 is energised, either by closure of switch 31 or switch 33, a sufficient length of time to rotate tube 17 through an angle of 180° from the position shown in FIG. 2, to the position shown in FIG. 1 in which the open end of tube 17 is presented upwardly. In this position, the freely falling chips C enter the concave open end of tube 17 and pass therethrough for delivery to container 22.

A deflector plate 35 on wall 11 above tube frame 13 extends downwardly and outwardly from the wall. Plate 35 has its lower edge positioned above and laterally of flanged ring 20, and deflects chips to prevent lodging in the region of the confined space between ring 20 and wall 11.

Advantages of the hereinabove described sampling apparatus will be more fully appreciated when it is considered that the wood chips as delivered by carloads vary greatly in size and shape. For example, chips may range in size from about one-inch square to about one-inch by six-inches. It is of course understood that sampling the chips in this state is not feasible, because the larger, outsized chips must be removed by screening to leave the lesser size chips for pulping. In the event larger chips did get past the screens, and assuming a cross section of chip flow in chute 10 includes a uniform distribution of chip sizes, the shorter chips will fall directly into the open probe as seen in FIG. 1; the longer chips close to wall 11 too will fall into the probe, generally striking an edge of the spherical wall portion 27, or an edge of the semi-cylindrical wall portion, to pivot into the probe. If a longer chip is predominantly beyond the same edge of the probe, of course, it will pivot away to continue falling through the chute.

A primary need for sampling the screened chips is to determine the undesirable bark content of a carload, and this is readily achieved since the bark is capable of passing through the screens into the chute along with the chips. Since a sample is quickly obtainable by the present apparatus for analysis, a carload can be rejected almost immediately if the bark content or other contaminant content is found to be excessive.

We claim:

1. Apparatus for sampling irregularly shaped and sized particulate material as it moves in a flow path having a vertical component, comprising:
   an open-ended tube extending at acute angularity with respect to the recited vertical component of the flow path of the material, one open end of the tube being in the path of flow at a level above the level of the other open end of the tube;
   material-collecting means communicating with said other open end of said tube;

an extension on said one open end of the tube comprising a generally semi-cylindrical wall section coaxial with said tube and having a generally quarter-spherical section on its free end, said wall sections being cooperatively disposed to form a concave material-receiving probe surface to one side of said tube and a convex material-deflecting surface substantially coextensive with and facing oppositely from said probe surface; and means for mounting said tube solely for rotation about its axis of curvature, selectively to position said extension to present said concave material-receiving probe surface upwardly for free passage of said material through said tube and delivery to said collecting means, or to position said extension to present said convex material deflecting surface upwardly thereby to deflect said material and prevent the recited delivery thereof.

2. Apparatus for sampling irregularly shaped and sized particulate material as it moves in a flow path having a vertical component and defined at least in part by an upwardly extending wall section, comprising:

an open-ended tube extending through said wall section at acute angularity with respect to the recited vertical component of the flow path of the material, one open end of the tube being in the path of flow at a level above the level of the other open end of the tube;

material-collecting means communicating with said other open end of said tube;

an extension on said one open end of the tube comprising a generally semi-cylindrical wall section coaxial with said tube and having a generally quarter-spherical wall section on its free end, said curved wall sections being cooperatively disposed to form a concave material-receiving probe surface to one side of said tube and a convex material-deflecting surface substantially coextensive with and facing oppositely from said probe surface;

means for mounting said tube solely for rotation about its axis of curvature, selectively to position said extension to present said concave material-receiving probe surface upwardly for free passage of said material through said tube and delivery to said collecting means, or to position said extension to present said convex material-deflecting surface upwardly thereby to deflect said material and prevent the recited delivery thereof.

3. Apparatus for sampling irregularly shaped and sized particulate material as it moves in a flow path defined at least in part by an upwardly extending wall section and having a vertical component, comprising:

an open-ended tube extending through said wall section at acute angularity with respect to the recited vertical component of the flow path of the material, one open end of the tube being in the path of flow at a level above the level of the other open end of the tube;

material-collecting means communicating with said other open end of said tube;

an extension on said one open end of the tube comprising a generally semi-cylindrical wall section coaxial with said tube and having a generally quarter-spherical wall section on its free end, said curved wall sections being cooperatively disposed to form a concave material-receiving probe surface to one side of said tube and a convex material-deflecting surface substantially coextensive with and facing oppositely from said probe surface; and means for mounting said tube solely for rotation about its axis of curvature, selectively to position said extension to present said concave material-receiving probe surface upwardly for free passage of said material through said tube and delivery to said collecting means, or to position said extension to present said convex material deflecting surface upwardly, thereby to deflect said material and prevent the recited delivery thereof, said means for mounting said tube comprising:

a tubular frame substantially coaxial with said tube, means mounting said frame in said upwardly extending wall section, and bushings in said frame rotationally supporting said tube.

4. Apparatus for sampling irregularly shaped and sized particulate material as it moves in a flow path having a vertical component, comprising:

an open-ended tube extending at acute angularity with respect to the recited vertical component of the flow path of the material, one open end of the tube being in the path of flow at a level above the level of the other open end of the tube;

material-collecting means communicating with said other open end of said tube;

an extension on said one open end of the tube comprising a generally semi-cylindrical wall section coaxial with said tube and having a generally quarter-spherical wall section on its free end, said wall sections being cooperatively disposed to form a concave material-receiving probe surface to one side of said tube and a convex material-deflecting surface substantially coextensive with and facing oppositely from said probe surface;

means for mounting said tube solely for rotation about its axis of curvature, selectively to position said extension to present said concave material-receiving probe surface upwardly for free passage of said material through said tube and delivery to said collecting means, or to position said extension to present said convex material deflecting surface upwardly thereby to deflect said material and prevent the recited delivery thereof; and means for rotating said tube comprising:

a motor having a shaft;

a worm on said shaft; and a worm gear disposed about said tube and being meshed with said worm.

5. Apparatus for sampling irregularly shaped and sized particulate material as it moves in a flow path defined at least in part by an upwardly extending wall section and having a vertical component, comprising:

an open-ended tube extending through said wall section at acute angularity with respect to the recited vertical component of the flow path of the material, one open end of the tube being in the path of flow at a level above the level of the other open end of the tube;

material collecting means communicating with said other open end of said tube;

an extension on said one open end of the tube comprising a generally semi-cylindrical wall section coaxial with said tube and having a generally quarter-cylindrical wall section on its free end, said curved wall sections being cooperatively disposed to form a concave material-receiving probe surface to one side of said tube and a convex material-deflecting surface substantially coextensive with and facing oppositely from said probe surface; and means for mounting said tube solely for rotation about its axis of curvature, selectively to position said extension to present said concave material-receiving probe surface upwardly for free passage of said material through said tube and delivery to said collecting means, or to position said extension to present said convex material deflecting surface upwardly thereby to deflect said material and prevent the recited delivery thereof, said means for mounting said tube comprising:

a tubular frame substantially coaxial with said tube; means mounting said frame in said upwardly extending wall section; bushings in said frame rotationally supporting said tube; and a flanged ring on said tube disposed in overlapping relation to an adjacent upper end of said tubular frame, thereby substantially sealing said tubular frame in prevention of entry of contaminants into said bearing means.

6. Apparatus for sampling particulate material as it moves through means defining a flow path having a vertical component, comprising:

means defining a tubular frame extending upwardly at acute angularity with respect to said vertical component of said flow path;

bearing means in said tubular frame;

a tube mounted in said bearing means for rotation within said frame, said tube including on an open end thereof in said flow path an extension comprising a generally semi-cylindrical wall section coaxial with said tube and having a generally quarter-spherical wall section on its free end, said wall sections being cooperatively disposed to form a concave material-receiving probe surface to one side of said tube and a convex material-deflecting surface substantially coextensive with and facing oppositely from said probe surface, the other end of said tube leading to sample-material collecting means;

a dust cap on said open end covering the upper end of said tubular frame;

a gear housing on the lower end of said frame;

a worm gear disposed about and on said tube;

a worm in said housing drivingly meshed with said worm gear and driven by a shaft extending into said housing;

a bearing surface on the lower face of said worm gear;

means on said gear housing presenting a thrust bearing for engagement by said face of said worm gear, in provision of axially directed support of said tube in said tubular frame; and means including a motor for driving said shaft to rotate said tube, selectively, between a pair of positions presenting said probe to receive particulate material or presenting said probe to deflect particulate material for passage or non-passage thereof, respectively, through said tube for collection.

7. Apparatus for sampling particulate material as it moves through means including an upwardly extending wall having an aperture and defining a flow path having a vertical component, comprising:

means defining a tubular frame mounted on said wall and extending upwardly through said aperture at acute angularity with respect to said vertical component of said flow path;

bearing means in said tubular frame;

a tube mounted in said bearing means for rotation within said frame, said tube including on an open end thereof in said flow path an extension comprising a generally semi-cylindrical wall section coaxial with said tube and having a generally quarter-spherical wall section on its free end, said wall sections being cooperatively disposed to form a concave material-receiving probe surface to one side of said tube and a convex material-deflecting surface substantially coextensive with and facing oppositely from said probe surface, the other end of said tube leading to provided sampled-material collecting means;

a dust cap on said open end covering the upper end of said tubular frame;

a gear housing on the lower end of said frame;

a worm gear disposed about and on said tube;

a worm in said housing drivingly meshed with said worm gear and driven by a shaft extending into said housing;

a bearing surface on the lower face of said worm gear;

means on said gear housing presenting a thrust bearing for engagement by said face of said worm gear, in provision of axially directed support of said tube in said tubular frame; and means including a motor for driving said shaft to rotate said tube, selectively, between a pair of positions presenting said probe to receive particulate material or presenting said probe to deflect particulate material for passage or non-passage thereof, respectively, through said tube for collection.

* * * * *